(12) United States Patent
Bernreuter

(10) Patent No.: US 6,226,540 B1
(45) Date of Patent: *May 1, 2001

(54) MEASURING PROCESS FOR BLOOD GAS ANALYSIS SENSORS

(76) Inventor: Peter Bernreuter, Alte Kirchheimerstrasse 38, D-73230 Nabern (Kirchheim) (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/325,841

(22) Filed: Jun. 4, 1999

Related U.S. Application Data

(63) Continuation-in-part of application No. 08/763,850, filed on Dec. 11, 1996, now Pat. No. 5,922,607.

(30) Foreign Application Priority Data

Dec. 13, 1995 (DE) ............................................. 195 46 502

(51) Int. Cl.⁷ .................................................... A61B 5/00
(52) U.S. Cl. ........................................... 600/323; 600/333
(58) Field of Search .................................. 600/310, 322, 600/323, 330, 333, 336

(56) References Cited

U.S. PATENT DOCUMENTS

| | | | |
|---|---|---|---|
| 4,807,631 | * 2/1989 | Hersh et al. | 600/323 |
| 5,595,176 | * 1/1997 | Yamaura | 600/323 |
| 5,922,607 | * 7/1999 | Bernreuter | 436/68 |

* cited by examiner

*Primary Examiner*—Eric F. Winakur
(74) *Attorney, Agent, or Firm*—Dennison, Scheiner, Schultz & Wakeman

(57) ABSTRACT

The invention relates to a measuring process, the purpose of which is to increase the measuring accuracy of pulse oxymeters and comparable optical devices which are used in vivo to ascertain oxygen saturation of arterial blood. The measuring process according to the invention is provided for the purpose of ascertaining oxygenation of arterial blood in tissue by evaluating the differential light attenuation at several wavelengths. It is characterized by the fact that light attentuation of at least one wavelength is determined in order to choose those calibration curves of several variables ($\Omega 1$, $\Omega 2$, . . . ) produced by different wavelength pairings with a minimized error in order to generate an output signal for the arterial blood oxygenation.

24 Claims, 2 Drawing Sheets

MEASURING PROCESS FOR BLOOD GAS ANALYSIS SENSORS

This application is a continuation-in-part of U.S. application Ser. No. 08/763,850 filed Dec. 11, 1996, now U.S. Pat. No. 5,922,607.

BACKGROUND OF THE INVENTION

The invention relates to a measuring process, the purpose of which is to increase the measuring accuracy of pulse oxymeters and comparable optical devices which are used in vivo to ascertain oxygen saturation of arterial blood.

According to the current prior art pulse oxymeters function on the basis that differing wavelengths blood attenuates light very differently depending upon the level of oxygenation. Pulse waves starting from the heart cause in the arterial blood vessel system a periodic fluctuation in the arterial blood content in the tissue. As a consequence, a periodic change in the light absorption (FIG. 1) can be registered between the light transmitter, whose radiation passes through the tissue, and the receivers, which are integrated in a pulse oxymetry sensor. The evaluation of the sensor signals is normally carried out at light wavelength of 660 and 940 nm by calculating the differential change of light absorption. It is possible to create a measured variable $\Omega$ (sometimes also referred to as R) which is obtained in the following manner or in a similar manner:

$$\Omega = \frac{\ln \frac{I_{min \lambda 1}}{I_{max \lambda 1}}}{\ln \frac{I_{min \lambda 2}}{I_{max \lambda 2}}}$$

The light intensities described in the formula represent the light intensities received in the receiver of the sensors used in pulse oxymetry. The measured variable $\Omega$ serves as a measurement for the oxygen saturation. The formation of a quotient in order to form the measured variable is intended to compensate any possible influences the haemoglobin content of the tissue, the pigmentation of the skin or the pilosity may have on the measurement of the oxygen saturation of arterial blood. (See also "Biomedizinische Technik" [Biomedical Technology] Volume 33, Supplementary volume 3, page 6 ff.:"Pulse oxymetrie: Stand und Entwicklung der Technik" [Pulse oxymtery: Status and developement of the technology"; Volume 35, Supplementary volume 1, page 38 ff. "Pulsoxymetrie" [Pulse oxymetry] by K Fortsner Institute for Biomedical Technology, Stuttgart). The influences of blood perfusion in the tissue, the pigmentation and pilosity are not taken into consideration in this measuring process.

When measuring oxygen saturation of arterial blood in the tissue in a range of 70 to 100% using light of wavelength 940 nm and 660 nm this also produces sufficiently accurate measured values. However, in order to measure lower oxygen saturation of arterial blood it is necessary to assume a strong influence on the measured variable $\Omega$ in particular caused by perfusion (i.e. blood content) (see: IEEE Photon Diffusion Analysis of the Effects of Multiple Scattering on Pulse Oximetry by Joseph M. Schmitt) and other optical parameters of tissue.

The dependency of the oxygen saturation of arterial blood $SaO_2$ on the variable $\Omega$ and the perfusion p can be written as follows (see also FIG. 2):

$$SaO_2 = f(\Omega, p)$$

Similar influences can be caused by pigmentation and pilosity of the skin or scattering and inhomogeneous tissue.

The technical problem resides in the fact that oxygen saturation of arterial blood must be determined in vivo using the process of pulse oxymetry without the perfusion, scattering and inhomogeneity in the tissue or pigmentation and pilosity of the skin influencing the measured result. For this reason, it is necessary to locate from the number of possible calibration curves, those curves which render it possible to determine in the most precise manner the oxygen saturation of arterial blood.

SUMMARY OF THE INVENTION

The invention relates to a method for determining the oxygenation level of blood in living tissue by evaluating the differential attenuation of light at several wavelengths. Light attenuation at at least one wavelength is determined in order to choose those calibration curves of several variables ($\Omega_1$, $\Omega_2$ . . . ) produced by different wavelength pairings with a minimized error in order to generate an output signal for the arterial blood oxygenation.

By measuring the light attenuation LA in the tissue, which can be determined by relating the intensity I registered in the receiver of the sensor to the initial intensity $I_0$ generated by the emitter for at least one wavelength, it is possible to select from a number of possible calibration curves those curves with which the oxygen saturation of the arterial blood can be determined in the most precise manner possible to improve considerably the accuracy of the measured values using pulse oxymeters particularly in cases where the oxygen N saturation of the blood is low. (Note: In this context "attenuation" means, that there is a defined relation between I(t) and $I_0(t)$).

The invention utilized calibration data $SaO_2$ vs. ($\Omega_1$, $\Omega_2$, . . . ) in order to produce calibration curves. These calibration curves are used in the method of the invention to obtain an output signal of $SaO_2$.

In a further embodiment, the measured value error can be minimized by measuring variables which are obtained from different wavelength pairings. Special choice of wavelength pairings allows to measure additional optical parameters if the calibration curve of this wavelength pairing is very sensitive to changes of the said parameter. Thus the best fitting calibration curves of wavelength pairings which are more sensitive to arterial oxygen changes can be chosen in order to determine the oxygen saturation.

In order to exclude the influence of pilosity and pigmentation, these parameters can be measured by determination of the attenuation between a receiver and emitter of light, which are close to one another (optical unit) (FIG. 4). By measuring the attenuation within further optical units and between these optical units optical parameters of the tissue can be determined without the influence of these parameters.

According to the above embodiments, measuring arterial oxygenation is accomplished by concurrently measuring the electrical activity of the subject whose blood oxygenation is determined in order to detect artefacts while registering the differential attenuation of blood.

A further method to reduce the error of $SaO_2$ is by characterizing the tissue inhomogeneity. This can be done by comparing the differential light absorptions $$\frac{I_{min\lambda 1}}{I_{max\lambda 1}}$$

at different distances of the light receivers and emitters.

DESCRIPTION OF THE PREFERRED EMBODIMENTS

Figure 1:
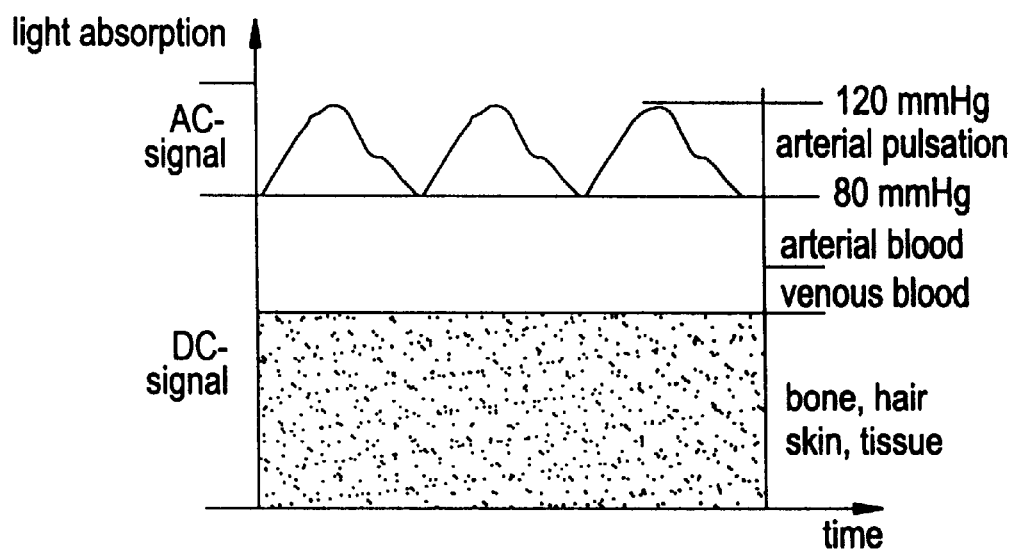
FIG. 1 is a diagram illustrating the change of light absorption with time.

The diagram of FIG. 1 shows the fundamental effect, on which pulse oxymetry and comparable methods to determine arterial blood oxygenation are based on. When measuring light absorption of tissue in vivo light absorption changes synchronously with every heart cycle. The diagram illustrates the change of light absorption versus time, which is caused by arterial pulsations that can be measured while systole and diastole. During systole and diastole the pressure on the arterial vessel system varies from 80 mmHg to 120 mmHg. The change of light absorption is called the AC signal. The DC signal, the time-invariant part of the light absorption, is caused by the non-pulsating part of the arterial blood, the venous blood, bone hair, skin, tissue and other constant absorbers versus time.

Figure 2:
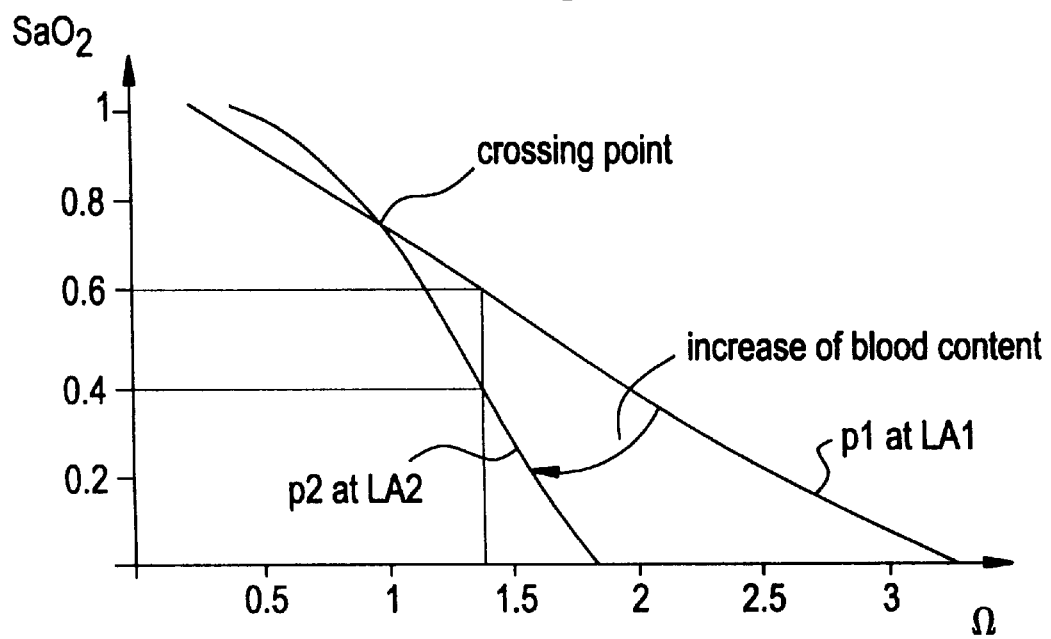
FIG. 2 is a diagram illustrating the dependency of oxygen saturation of arterial blood; on blood content

FIG. 2 shows two calibration curves in a diagram with SaO$_2$ vs. Ω. One diagram is marked with the label "p1 at LA1". This means that this calibration curve is only valid for a special level of perfusion (blood content) which can be measured with an optical system. The optical system can measure the light attenuation LA1 which is equivalent to perfusion p$_1$. The second calibration curve is characterized by the perfusion p$_2$ at LA2. The arrow between these two calibration curves indicates how the curves change their shape when perfusion increases. There is one point, where SaO$_2$ is independent of perfusion, that is the crossing point. Additionally there are dotted lines in the diagram at SaO$_2$= 0.6, SaO$_2$=0.38 and Ω=1.4. If an optical system determines only Ω without registering the light attenuation, this would result in a maximum error of 0.224 SaO$_2$ (SaO$_2$ at p1–SaO$_2$ at p1 with Ω=1.4).

Figure 3:
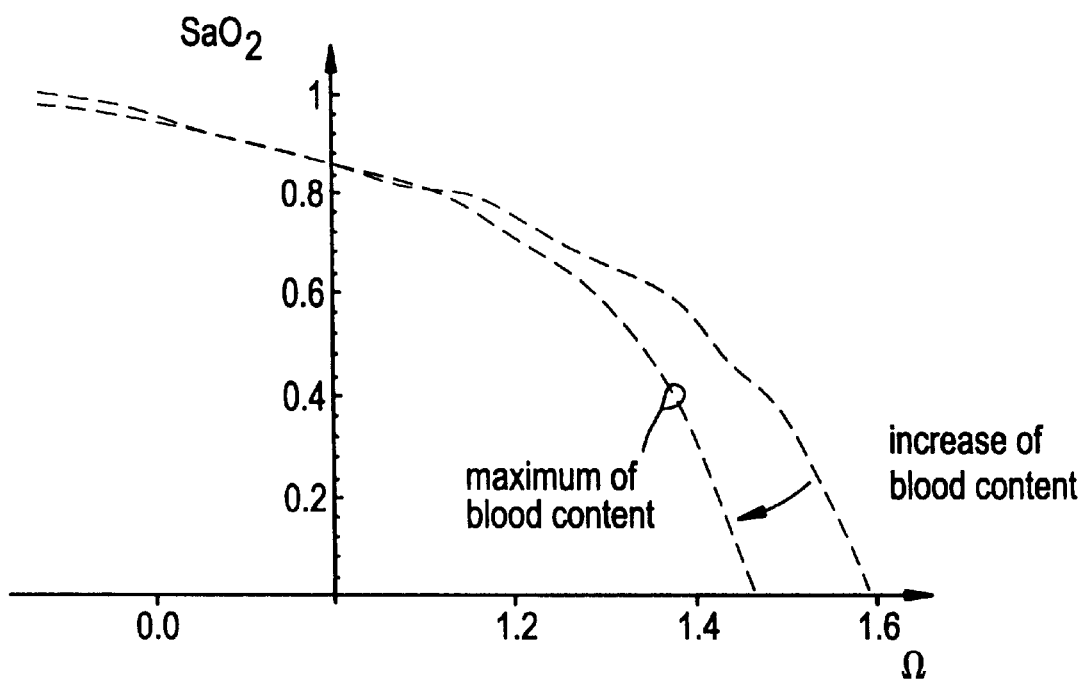
FIG. 3 shows two calibration SaO$_2$ vs. Ω) which depend at low oxygenation mainly or blood content.

FIG. 3 shows two calibration curves which depend on blood content of tissue. The arrow shows how curves will change when blood content increases. Ω is evaluated in this example from the wavelengths 730 nm and 660 nm. When SaO$_2$ is below 0.5 the calibration curves depend rather on changes of blood content than on changes of SaO$_2$. This effect can be used to measure blood content in tissue in order to choose the calibration curve of warelength pairings with a minimum of error of SaO$_2$.

Figure 4:
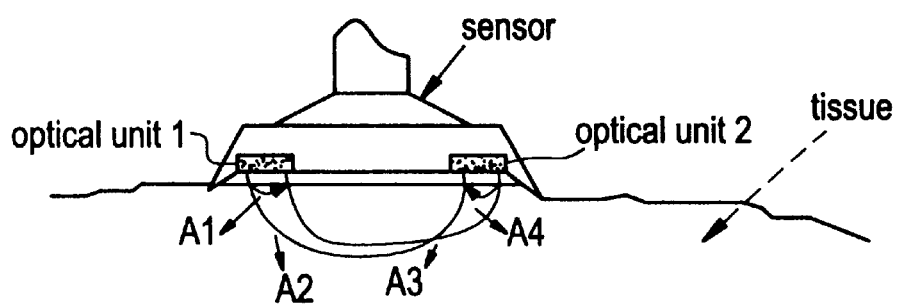
FIG. 4 shows a pulse oxymetry sensor according to the invention.

FIG. 4 shows a pulse oxymetry sensor on the upper part of the figure which is placed on tissue. The sensor contains two optical units which consist of a light emitter and receiver.

The arrows A1, . . . A4 show how light passes from light emitters to detectors through tissue. A1 stands representative for light, which is emitted in the optical unit one and detected in unit one. A2 is emitted in optical unit 1 one and detected in unit 2. A4 is emitted in unit 2 and detected in unit 2 and A3 is emitted in unit 2 and detected in unit 1.

EXAMPLE 1

Arterial oxygenation of blood in tissue depends on different optical parameters. FIG. 2 shows how calibration curves change, when blood content increases for a special wavelength pairing (about 660 nm and about 940 nm, qualitatively, where "about" is generally defined as ±60 nm)

After light attenuation, which corresponds to different blood contents in the tissue is determined, the calibration curve with the minimal error is chosen. Thus, if the measured light attenuation is LA1 and the Ω is 1.4, the output signal for Sao$_2$ is 0.6 and not 0.38 for the calibration curve at LA2.

EXAMPLE 2

FIG. 3 shows a diagram with a pairing of wavelength (730 nm and 660 nm), whose calibration curves depend on optical parameters of tissue (here blood content) but not on the arterial oxygenation for SaO$_2$ values below 50%. This effect is used to choose the calibration curve of a second wavelength pairing (see FIG. 2) with the minimal error for oxygenations. This means that if the estimation of a wavelength pairing for SaO$_2$ produces an output of SaO$_2$=0.30 and Ω for the calibration curves in FIG. 3 is 1.4, that blood content in tissue must be at a maximum. Therefore the calibration curve for the maximum of blood content will be chosen.

EXAMPLE 3

In order to exclude the influence of pilosity an pigmentation, while determining optical parameters of tissue all light attenuations A1, . . . , A4 (see FIG. 4) between the two optical units are determined.

The light attenuation LA of the tissue alone could be calculated as follows:

$$LA=(A2+A3-A1-A4)/2$$

This correlation is also very helpful to detect haematoms, which could increase the error of the output variable SaO$_2$.

EXAMPLE 4

If pigmentation and pilosity of the skin is dense, perfusion can be determined by measuring, for example, two isobestic points of light wavelength, such as 560 and 805 nm. For these light attenuations, the following is valid:

$$LA_{580}=\delta_{pig} \cdot \alpha_{pig550}+\delta_{blood} \cdot \alpha_{blood560}$$

$$LA_{805}=\delta_{pig} \cdot \alpha_{pig805}+\delta_{blood} \cdot \alpha_{blood805}$$

As the absorption coefficients α of blood, pigmentation and pilosity are known from attenuation, the measurement for blood content or perfusion $\delta_{blood}$ can be determined.

EXAMPLE 5

If three light wavelengths about 660 nm, about 740 nm and about 940 nm are used, the following two measurement variables can be constituted:

$$\Omega_1 = \frac{\ln\left(\frac{I_{min}}{I_{max}}\right)_{660\,nm}}{\ln\left(\frac{I_{min}}{I_{max}}\right)_{940\,nm}} \quad \text{and} \quad \Omega_2 = \frac{\ln\left(\frac{I_{min}}{I_{max}}\right)_{740\,nm}}{\ln\left(\frac{I_{min}}{I_{max}}\right)_{940\,nm}}$$

During measurement, when a value 1 is obtained for $\Omega_1$, it can be assumed with high accuracy that the oxygen saturation is approximately 75% (according to FIG. 3), since at this point the group of calibration curves intersects. The intersection point of the group of curves for $\Omega_2$ is also at a value of approximately 75% (according to FIG. 3). The measurement accuracy can be increased for the pulsoxymetric measurement by weighting an output signal for the oxygen saturation higher than $\Omega$ at high saturation values, and $\Omega_2$ higher than $\Omega_1$ at low saturation values.

What is claimed is:

1. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different blood flow;
   b) measuring said light received passing through said tissue at said plurality of wavelengths at said instants of time;
   c) calculating a plurality of ratios of differential attenuation vs. time, $\Omega_i$ corresponding to $$\Omega_i = \frac{\ln(i_{min}/i_{max})_a}{\ln(i_{min}/i_{max})_b}$$

for each wavelength pair i=a,b of different frequencies, wherein at least one wavelength pairing is selected based on optical tissue parameters, sufficient wavelength pairings and calibration curves of SaO2 v. $\Omega_i$ have been empirically made such that the calibration curves are chosen for $\Omega_i$ depending on optical tissue parameters to minimize error in producing an output signal indicative of level of arterial oxygenation;
   d) calculating at least one attenuation ratio $LA_j$ through said tissue for at least one wavelength, where $LA_j$ corresponds to:

$LA_j$=ln (light intensity received/light intensity emitted);

using calibration data of $SaO_2$ v. $\Omega_i$ for at least one said $LA_j$; and
   f) computing the level of oxygenation by comparing measured data with the calibration data.

2. The method of claim 1, wherein one of the wavelength pairings is at isobestic points at 560 and at 805 nm.

3. The method of claim 1, wherein one of the wavelength pairings is at about 660 and about 740 nm.

4. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different blood flow;
   b) measuring said light received passing through said tissue at said plurality of wavelengths at said instants of time;
   c) calculating one ratio of differential attenuation vs. time, $\Omega_i$ corresponding to $$\Omega_i = \frac{\ln(i_{min}/i_{max})_a}{\ln(i_{min}/i_{max})_b}$$

for each wavelength pair i=a,b of different frequencies;
   d) calculating at least one attenuation ratio $LA_j$ through said tissue for at least one wavelength, where $LA_j$ corresponds to:

$LA_j$=ln (light intensity received/light intensity emitted);

e) using stored calibration data of $SaO_2$ v. $\Omega_i$ at least one said $LA_j$; and
   f) computing the level of oxygenation by comparing measured data with the calibration data.

5. The method of claim 4, wherein the wavelength pairings are about 660 and about 940 nm and about 730 and about 940 nm.

6. The method of claim 1 or 4, wherein at least two emitter/detector pairs are utilized, comprising the steps of:
   g) measuring light emitted in a first optical unit and detected in a first optical unit;
   h) measuring light emitted in said first optical unit and detected in a second optical unit;
   i) measuring light emitted in said second optical unit and detected in said first optical unit;
   j) measuring light emitted in said second optical unit and detected in said second optical unit;
   k) weighting light attenuations between detectors and emitters to generate LA;
   l) repeating steps g)–k) for more than two optical units and weighting generated values of LA in order to generate a resulting light attenuation; and
   m) using the determined light attenuation to choose an associated calibration curve.

7. The method of claim 1 or 4, wherein at least two emitter/detector optical units are utilized, comprising the steps of:
   n) measuring light emitted in a first optical unit and detected in said first optical unit A1;
   o) measuring light emitted in said first optical unit and detected in a second optical unit A2;
   p) measuring light emitted in said second optical unit and detected in said first optical unit A3;
   q) measuring light emitted in said second optical unit and detected in said second optical unit A4;
   r) computing the optical constitution of said tissue alone relating to the measured light attenuation by weighting and accumulating the light attenuations between the optical units (A2, A3) and subtracting therefrom the weighted and accumulated light attenuations within the optical units (A1, A4); and
   s) repeating steps n)–r) for any other sets of optical unit pairs, and an appropriate weighting in accordance with step r); and
   t) generating an output signal for the arterial oxygen saturation depending on LA or a set of LA values.

8. The method of claim 7, wherein light attenuation is defined as $LA_k$=ln (light intensity received).

9. The method of claim 1 or 4, wherein said attenuation ratio $LA_j$ is calculated as:

$$LA_j = \ln \frac{\text{light intensity received}}{\text{light intensity emitted}}.$$

10. The method of claim 1 or 4, wherein $LA_j$ depends on change of light intensity versus time emitted by at least one emitter $I_n(t)$ and on change of light intensity received by at least one receiver $I(t)$ which receives the light of said at least one emitter.

11. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different blood flow;
   b) measuring said light received passing through said tissue at said plurality of wavelengths at said instants of time;
   c) calculating a plurality of ratios of differential attenuation vs. time, $\Omega_i$ corresponding to $$\Omega_i = \frac{\ln(i_{min}/i_{max})_a}{\ln(i_{min}/i_{max})_b}$$

for each wavelength pair i=a,b of different frequencies; and
   d) computing oxygenation level depending on multidimensional calibration data of $SaO_2$ vs. $\Omega_i$ for different ratios of differential attenuation vs. time calculated in step c).

12. The method of claim 11, additionally comprising using said calibration data to prepare calibration curves, and computing the level of oxygenation by obtaining the data from the calibration curves.

13. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different blood flow;
   b) measuring said light received passing through said tissue at said plurality of wavelengths at said instants of time;
   c) calculating a plurality of ratios of differential attenuation vs. time, $\Omega_i$ corresponding to $$\Omega_i = \frac{\ln(i_{min}/i_{max})_a}{\ln(i_{min}/i_{max})_b}$$

for each wavelength pair i=a,b of different frequencies;
   d) selecting at least one wavelength pairing based on optical tissue parameters $\Omega_j$;
   e) selecting sufficient wavelength pairings and calibration curves of $SaO_2$ vs. $\Omega_i$ which were empirically made and dependent on optical tissue parameters which correspond to $\Omega_j$;
   f) computing the level of oxygenation depending by comparing measured data with the calibration data; and
   g) minimizing error in producing an output signal indicative of level of arterial oxygenation by using calibration curves of $SaO_2$ v. $\Omega_j$.

14. The method of claim 1, 4, 11 or 13, wherein one of the wavelength pairings is at isobestic points 560 and 805 nm.

15. The method of claim 1, 4, 11 or 13, wherein one of the wavelength pairings is at about 660 and about 740 nm.

16. The method of claim 1, 4, 11 or 13, additionally comprising calculating $\Omega_i$ as:

$$\Omega_1 = \frac{\frac{\text{change of intensity at freq. } a}{\text{total light intensity at freq. } a}}{\frac{\text{change of intensity at freq. } b}{\text{total light intensity at freq. } b}}.$$

17. The method of claim 11 or 13, wherein the step of determining differential attenuation vs. time is accompanied by a concurrent measurement of electrical activity of the heart.

18. The method of claim 1, 4, 11 or 13, wherein tissue inhomogeneity $LAT_m$ is evaluated by measuring:
   u) differential attenuation, $dLA_j$, at a first distance between emitter and detector;
   v) differential attenuation, $dLA_k$, at a second distance between emitter and detector;
   w) calculating $LAT_m = dLA_j/dLA_k$;
   x) repeating steps u)–x) for further pairs of emitter/detector distances;
   y) generating an output signal for the arterial oxygen saturation depending on $LAT_m$.

19. The method of claim 18, wherein the differential attenuation is defined as:
   dLA=change in light absorption at a distance j,k within a time interval $\Delta t$.

20. The method of claim 18, additionally comprising using said calibration data to prepare calibration curves, and computing the level of oxygenation by obtaining the data from the calibration curves.

21. The method of claim 1, 4, 11 or 13, wherein in step c), an output signal indicative of level of arterial oxygenation is generated by an additional step comprising selecting a function which depends on at least one of the parameters $\Omega$ values based on optical tissue parameters, light attenuations and differential light absorptions, and approximates empirical data of $SaO_2$ vs. $\Omega_i$ and said parameters.

22. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different blood flow;
   b) measuring said light received passing through said tissue at said plurality of wavelengths at said instants of time;
   c) calculating a plurality of ratios of differential attenuation vs. time, $\Omega_i$ corresponding to $$\Omega_i = \frac{\ln(i_{min}/i_{max})_a}{\ln(i_{min}/i_{max})_b}$$

for each wavelength pair i=a,b of different frequencies;
   d) approximating a function depending on $\Omega$ values based on optical tissue parameters and arterial blood oxygenation obtained from empirical data in order to minimize error on the output signal for the arterial blood oxygenation; and
   e) generating and output signal based on the function obtained by step d) and the measured $\Omega$ values.

23. Apparatus for determining oxygen saturation of arterial blood in living tissue by pulse oximetry, comprising:

means for emitting light through living tissue at a plurality of wavelengths at different instants of time with different blood flows through the tissue;

means for measuring the light emitted and passing through the tissue at said plurality of wavelengths at said instants of time; and means for computing the level of oxygen saturation depending on data measured and previously obtained calibration data;

wherein said means for emitting and means for measuring comprise at least two optical units, each of said optical units comprising a light emitter and light receiver.

24. Apparatus for determining oxygen saturation of arterial blood in living tissue by pulse oximetry, comprising:

means for emitting light through living tissue at a plurality of wavelengths at different instants of time and different blood flows;

means for measuring light passing through the tissue at said plurality of wavelengths and instants of time; and means for computing oxygen saturation based on data obtained by said measuring and previously obtained calibration data;

wherein said means for measuring comprises a sensor which measures at least three wavelengths, thereby enabling said means for computing to use at least two values of differential attenuation vs. time $\Omega$.

* * * * *

UNITED STATES PATENT AND TRADEMARK OFFICE
CERTIFICATE OF CORRECTION

| | | |
|---|---|---|
| PATENT NO. | : 6,226,540 B1 | Page 1 of 1 |
| DATED | : May 1, 2001 | |
| INVENTOR(S) | : Peter Bernreuter | |

It is certified that error appears in the above-identified patent and that said Letters Patent is hereby corrected as shown below:

Title page,
Item [76] Inventor: correct the inventor information to read as follows:
-- Peter Bernreuter, Gartenstrasse 12, D-73230 Nabern Kirchheim, DE --;

Item [30] Foreign Application Priority Data, insert: -- Jan. 3, 1996 (PCT) EP 96/00003 --

Signed and Sealed this

Twelfth Day of March, 2002

Attest:

Attesting Officer

JAMES E. ROGAN
*Director of the United States Patent and Trademark Office*